US006218153B1

(12) United States Patent
Sklar et al.

(10) Patent No.: US 6,218,153 B1
(45) Date of Patent: Apr. 17, 2001

(54) TARGET DNA AMPLIFICATION BY MIPC AND PCR

(75) Inventors: Jeffrey L. Sklar, Chestnut Hill, MA (US); Douglas T. Gjerde, Saratoga, CA (US); Kimberly A. Lamb, Omaha, NE (US); Christopher Hanna, Somerville, MA (US)

(73) Assignee: Transgenomic, Inc., San Jose, CA (US)

( * ) Notice: Subject to any disclaimer, the term of this patent is extended or adjusted under 35 U.S.C. 154(b) by 0 days.

(21) Appl. No.: 09/311,116

(22) Filed: May 13, 1999

Related U.S. Application Data

(63) Continuation-in-part of application No. 09/183,573, filed on Oct. 30, 1998, now abandoned.
(60) Provisional application No. 60/064,437, filed on Oct. 31, 1997.

(51) Int. Cl.$^7$ .............................. C12Q 1/68; C12P 19/34; C07H 21/04; B01D 15/00
(52) U.S. Cl. ......................... 435/91.2; 435/6; 536/22.1; 536/25.4; 210/635; 210/198.2
(58) Field of Search ................................ 536/25.4, 22.1; 435/6, 91.2; 210/635, 198.2

(56) References Cited

U.S. PATENT DOCUMENTS

| 5,203,992 | 4/1993 | Drouen ............................... 210/198.2 |
| 5,508,204 | 4/1996 | Norman ............................... 436/161 |
| 5,795,976 | * 8/1998 | Oefner et al. . |
| 5,969,228 | 10/1999 | Gorenstein ......................... 73/23.22 |

FOREIGN PATENT DOCUMENTS

| WO 99/47710 | 9/1999 | (WO) ............................... C12Q/1/68 |

OTHER PUBLICATIONS

Arnold, et al. A Highly Sensitive, Fast, and Economical Technique for Mutation Analysis in Hereditary Breast and Ovarian Cancers, Human Mutation, 14:333–339, (1999).
Belenky et al. High–Throughput Biopolymer Desalting Prior to Mass Spectrometry Using 96–Well Solid–Phase Extraction Plates, Abstract No. P9, DNA 2000 International Symposium, Jun. 1–3, 2000, Boston, Mass.
Brossette et al. A Program for Selecting DNA Fragments to Detect Mutations by Denaturing Gel Electrophoresis Methods, Nucleic Acids Res., 22:4321–4325, (1994).
Gioradano et al. Identification by Denaturing High–Performance Liquid Chromatography of Numerous Polymorphisms in a Candidate Region for Multiple Sclerosis Susceptibility, Genomics, 56:247–253, (1999).

Gross et al. A Comparison of BRCA1 Mutation Analysis by Direct Sequencing, SSCP and DHPLC, Hum. Genet., 105:72–78, (1999).
Huber et al. High–Resolution Liquid Chromatography of DNA Fragments on Non–Porous Poly (Styrene–Divinylbenzene Particles), Nucleic Acids Research, vol. 21, No. 5, 1061–1066, 1993.
Huber et al. High–Resolution Liquid Chromatography of Oligonucleotides on Nonporous Alkylated Styrene–Divinylbenzene Copolymers, Analytical Biochemistry, 212, 351–358, (1993).
Huber, Christian, High–Performance Liquid Chromatographic Separation of Detritylated Oligonucleotides on Highly Cross–Linked Poly (Styrene–Divinylbenzene) Particles, Journal of Chromatography, 599, 113–118, (1992).
Jones et al. Optimal Temperature Selection for Mutation Detection by Denaturing HPLC and Comparison to Single–Stranded Conformation Polymorphism and Heteroduplex Analysis, Clinical Chem., 45–48, 1999.
Oefner et al. High–Resolution Liquid Chromatography of Fluorescent Dye–Labeled Nucleic Acids, Analytical Biochemistry, 223, 001–008, (1994).
Oefner et al, High Resolution Liquid Chromatography of Nucleic Acids, American Laboratory, 28C—28J, (1994).
Oefner et al. DNA Mutation Detection Using Denaturing High–Performance Liquid Chromatography (DHPLC), Current Protocols in Human Genetics, 7.10.1–7.10.12, 1998.
Marlowe et al. A Method for Detection and Quantitation of PCR Template in Environmental Samples by High Performance Liquid Chromatography, Journal of Microbiological Methods, 28, 45–53, (1997).

* cited by examiner

Primary Examiner—Kenneth R. Horlick
Assistant Examiner—Jeffrey Siew
(74) Attorney, Agent, or Firm—William B. Walker

(57) ABSTRACT

A method for detecting a putative mutant DNA in a sample of DNA includes the steps of amplifying the sample of DNA using PCR; hybridizing the amplified sample to form a mixture of homoduplexes and heteroduplexes; separating the mixture into fractions by Denaturing Matched Ion Polynucleotide Chromatography; and blind collecting the eluted fractions at a retention time corresponding to the retention time of the heteroduplex. The DNA in the blind collected fractions can be PCR amplified to obtain an increased amount of heteroduplex relative to homoduplex. The method is useful for determining the remission status of a patient in which the tissue-derived DNA sample contains a large background of wild type or where the putative mutant DNA is below the limit of detection.

30 Claims, 2 Drawing Sheets

TARGET DNA AMPLIFICATION BY MIPC AND PCR

CROSS REFERENCE TO RELATED CO-PENDING APPLICATION

This application is a continuation in part of U.S. patent application Ser. No. 09/185,573 filed Oct. 30, 1998 (abandoned).

This application is a regular U.S. patent application under 35 U.S.C. §111(a) and 37 C.F.R. 1.53(b) and claims priority from the following co-pending, commonly assigned provisional applications, each filed under 35 U.S.C. §111(b):

Ser. No. 60/064,437 filed October 31, 1997
Ser. No. 60/103,313, filed October 6, 1998, and the following co-pending commonly assigned non-provisional applications, each filed under 53 U.S.C. §111:

Ser. No. 09/039,061 filed March 13, 1998 (pending)
Ser. No. 09/058,337 filed April 10, 1998 (now abandoned)
Ser. No. 09/058,580 filed April 10, 1998 (abandoned)
Ser. No. 09/129,105 filed August 4, 1998. (pending)

The entire contents of the above-listed pending application are hereby incorporated by reference.

FIELD OF THE INVENTION

The present invention concerns a chromatographic method for detection of mutations in nucleic acids.

BACKGROUND OF THE INVENTION

The early diagnosis of certain diseases, especially cancer, can save many lives. In the case of cancer, and other diseases of genetic origin, early detection often depends on the availability of an appropriate analytical method which can accurately and reliably detect a putative mutation in DNA samples. This problem is exacerbated by the fact that such samples generally contain a very small population of cells containing mutant DNA in the presence of a very large predominantly normal cell population containing wild type DNA. Any separation technique which is capable of detecting mutant DNA in the presence of wild type would fail under these circumstances because the concentration of mutant DNA is simply too low to be detected relative to wild type. That is to say, the concentration of mutant DNA may be too low to detect in absolute terms. Alternatively, the concentration of mutant DNA may be sufficient to detect, but will be completely obscured because of the very large relative amount of wild type in the sample.

Increasing the amount of mutant DNA by PCR amplification of the sample would not solve the problem described above. The mutant and wild type DNA in the sample are very similar. In fact, their sequence may differ by only a single base pair. Therefore, the primers which would be used to amplify the mutant DNA would also amplify the wild type since both are present in the sample. As a result, the relative amounts of mutant and wild type DNA would not change.

Following radiation or chemotherapy, cancer patients are monitored for the presence of residual cancer cells to determine whether the patients are in remission. The effectiveness of these treatments can be monitored if small levels of residual cancer cells could be detected in a predominantly large wild type population. Traditionally, the remission status is assessed by a pathologist who conducts histological examination of tissues samples. However, these visual methods are largely qualitative, time-consuming, and costly. At best, the sensitivity of these methods permits detection of about 1 cancerous cell in 100 cells.

Analysis of DNA samples has historically been done using gel electrophoresis. Capillary electrophoresis has also been used to separate and analyze mixtures of DNA. However, these methods cannot distinguish point mutations from homoduplexes having the same base pair length.

Gel based analytical methods, such as denaturing gradient gel electrophoresis and denaturing gradient gel capillary electrophoresis, can detect mutations in heteroduplex DNA strands under "partially denaturing" conditions. The term "partially denaturing" means the separation of a mismatched base pair (caused by temperature, pH, solvent, or other known factors) in a DNA double strand while the remainder of the double strand remains intact. However, these gel based techniques are operationally difficult to implement and require highly skilled personnel. In addition, the analyses are lengthy and require a great deal of set-up time. A denaturing capillary gel electrophoresis analysis of a 90 base pair fragment takes more than 30 minutes and a denaturing gel electrophoresis analysis may take 5 hours or more. The long analysis time of the gel methodology is further exacerbated by the fact that the movement of DNA fragments in a gel is inversely proportional, in a geometric relationship, to their length. Therefore, the analysis time of longer DNA fragments can be often be untenable. Sample recovery of DNA fragments separated on a gel is difficult and time consuming, requiring specialized techniques.

In addition to the deficiencies of denaturing gel methods mentioned above, these techniques are not always reproducible or accurate since the preparation of a gel slab and running an analysis can be highly variable from one operator to another. As a result, the mobility of a DNA fragment is often different on different gel slabs and even in one lane, compared to another on the same gel slab. The problems and deficiencies of gel based DNA separation methods are well known in the art and are described in "Laboratory Methods for the Detection of Mutations and Polymorphisms", ed. G. R. Taylor, CRC Press (1997).

SUMMARY OF THE INVENTION

It is an object of the present invention to provide a sensitive and reproducible method which would enable the detection of small amounts of mutant DNA in the presence of a relatively large amount of wild type DNA, wherein such mutations would otherwise go undetected. It is a further object of the invention to provide an analytical method which is reproducible, reliable, inexpensive, can be automated and can be used for high throughput sample screening.

In one aspect, the present invention is a method for detecting a putative mutant DNA in a sample of DNA, the method including the steps of (a) amplifying the sample of DNA using PCR, (b) hybridizing the amplified sample to form a mixture of homoduplexes and heteroduplexes, (c) separating the product of step (b) into fractions by Denaturing Matched Ion Polynucleotide Chromatography, and (d) blind collecting the fractions from step (c) at a retention time corresponding to the retention time of the heteroduplex. The method preferably includes amplifying the fractions collected in step (d) using PCR to obtain an increased amount of heteroduplex relative to homoduplex. The method can also include repeating steps (a) through (d); in a preferred method these steps are repeated until the relative amount of mutant to wild type DNA is increased by an enhancement factor of at least 10 to 1000. The DNA sample can contain a large background of wild type. The putative mutant DNA can be below the limit of detection. The identity of the heteroduplex can be confirmed using standard methods. In a preferred embodiment, the DNA sequence of the wild type DNA and the mutant DNA are known. In a typical analysis using the method of the invention, the mutant DNA differs from wild type DNA by at least one base pair. In a preferred embodiment, the same PCR primers are used to amplify both the mutant DNA and the wild type DNA in the sample. In another preferred embodiment, the retention time used in the blind collection of the heteroduplex in step (d) was previously determined from a reference standard. A preferred reference standard is obtained by separating a standard mixture of homoduplex and heteroduplex, having the same base pair sequence as the sample, by Matched Ion Polynucleotide Chromatography.

In a preferred embodiment of the invention, the separation of the product by Denaturing Matched Ion Polynucleotide Chromatography is effected with an MIPC column containing a stationary phase separation media, and the column is treated before the separating step with a solution for removing any residual DNA from prior separations. For example, the column can be treated before the separating step with from 50 μL to 1 ml of tetrasodium EDTA adjusted to a pH of 13 with sodium hydroxide. Other treatments for washing a column can also be used alone or in combination with those indicated hereinabove. These treatments include exposing the separation medium to high concentrations of organic solvent (e.g., up to 100% acetonitrile) or exposing the medium to denaturants such as urea or formamide. The column can also be treated by reverse flushing with a washing solution.

In another aspect, the present invention is a method for screening a tissue sample for cancerous cells by detecting a putative mutant DNA in the DNA of the sample, the method including the steps of (a) amplifying the sample DNA using PCR, (b) hybridizing the amplified sample to form a mixture of homoduplexes and heteroduplexes, (c) separating the product of step (b) into fractions by Denaturing Matched Ion Polynucleotide Chromatography, and (d) blind collecting the fractions from step (c) at a retention time corresponding to the retention time of the heteroduplex.

The method preferably includes amplifying the fractions collected in step (d) using PCR to obtain an increased amount of heteroduplex relative to homoduplex. The method can also include repeating steps (a) through (d); in a preferred method these steps are repeated until the relative amount of mutant to wild type DNA is increased by an enhancement factor of at least 10 to 1000. The DNA sample can contain a large background of wild type. The putative mutant DNA can be below the limit of detection. The identity of the heteroduplex can be confirmed using standard methods. In a preferred embodiment, the DNA sequence of the wild type DNA and the mutant DNA are known. In a typical analysis using the method of the invention, the mutant DNA differs from wild type DNA by at least one base pair. In a preferred embodiment, the same PCR primers are used to amplify both the mutant DNA and the wild type DNA in the sample. In another preferred embodiment, the retention time used in the blind collection of the heteroduplex in step (d) was previously determined from a reference standard. A preferred reference standard is obtained by separating a standard mixture of homoduplex and heteroduplex, having the same base pair sequence as the sample, by Matched Ion Polynucleotide Chromatography.

DETAILED DESCRIPTION OF THE INVENTION

Figure 1:
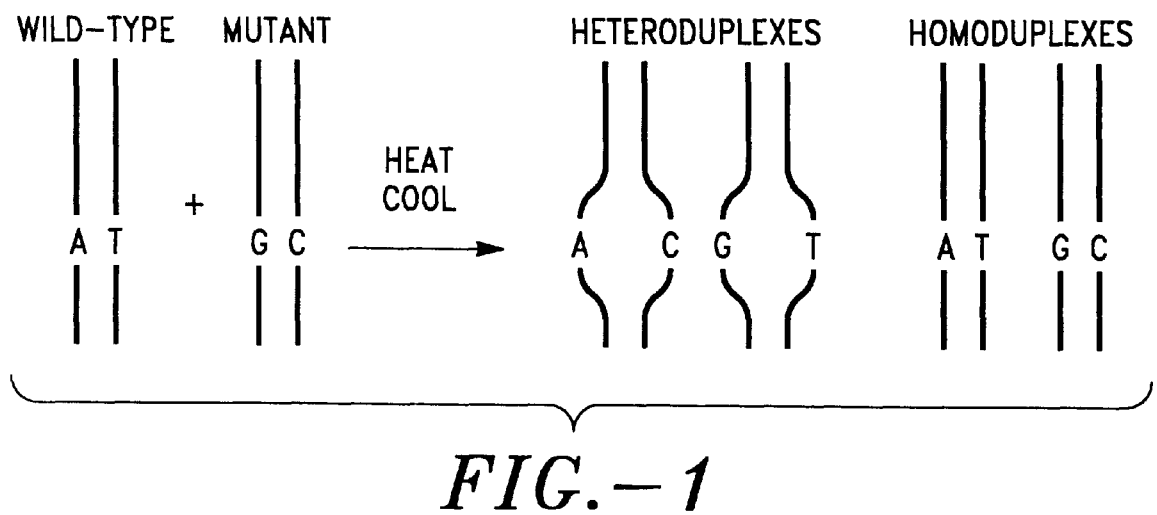
FIG. 1 is a schematic representation of hybridization of wild type DNA strand with homozygous mutant strand showing the production of two homoduplexes and two heteroduplexes.

The present invention relates, therefore, to the unambiguous detection and identification of very small amounts of heteroduplex fragments containing mutant DNA in the presence of a relatively very large amount of known wild type using a recently developed chromatographic method called Denaturing Matched Ion Polynucleotide Chromatography (DMIPC), a method analogous to Matched Ion Polynucleotide Chromatography (MIPC).

MIPC separates DNA fragments based on their base pair length (U.S. Pat. No. 5,585,236 to Bonn (1996); Huber, et al., *Chromatographic* 37:653 (1993); Huber, et al., *Anal. Biochem.* 212:351 (1993)). These references and the references contained therein are incorporated herein in their entireties. When MIPC analyses are performed at partially denaturing temperature, the process is called DMIPC. These separation methods obviate the deficiencies of gel based methods and make possible the collection and identification of mutant DNA fragments whose concentration relative to wild type is small, and may be below the detection limits of a detector. Alternatively, MIPC and DMIPC make possible the collection and identification of mutant fragments which would be obscured by a relatively large amount of wild type in a sample. This method will be discussed in detail herein below.

The term "Matched Ion Polynucleotide Chromatography" as used herein is defined as a process for separating single and double stranded polynucleotides using non-polar separation media, wherein the process uses a counter-ion agent, and an organic solvent to release the polynucleotides from the separation media. MIPC separations are complete in less than 10 minutes, and frequently in less than 5 minutes. MIPC systems (WAVE™ DNA Fragment Analysis System, Transgenomic, Inc. San Jose, Calif.) are equipped with computer controlled ovens which enclose the columns and sample introduction areas.

MIPC uses unique non-polar separation media which comprises organic polymers, silica media having a non-polar surface comprising coated or covalently bound organic polymers or covalently bound alkyl and/or aryl groups, and continuous non-polar separation media, i.e., monolith or rod columns such as non-polar silica gel or organic polymer. The separation media used in MIPC can be porous or non-porous. A detailed description of the MIPC separation process, MIPC separation media, and MIPC systems is found in U.S. Pat. No. 5,772,889 (1998) to Gjerde and in co-pending U.S. patent applications Ser. Nos. 09/058,580 filed Mar. 10, 1998; (abandoned); 09/058,337 filed Mar. 10, 1998; (abandoned); 09/081,040 filed May 18, 1998 (now U.S. Pat. No. 5,947,742); 09/080,547 filed May 18,1998

(now U.S. Pat. No. 6,017,457); and in the U.S. patent application Ser. No. 09/169,440 filed Oct. 9, 1998. MIPC systems and separation media are commercially available (Transgenomic, Inc. San Jose, Calif.). The entire MIPC analysis can be automated by means of a desk top computer and a sample auto-injector. Analytical data for each sample can be analyzed in real time, or collected and stored in a computer memory device for analysis at a later time.

The use of MIPC at partially denaturing temperature, i.e., DMIPC, to detect mutations has been described in a co-pending U.S. patent application Ser. No. 09/129,105 filed Aug. 4, 1998. This application and the references contained therein are incorporated herein in their entireties.

An important requirement for effective blind collections according to this invention is the absence from the separation media of any DNA fragments or other contaminants from prior separations. One procedure for insuring this prerequisite is cleaning the column after each separation with a suitable cleaning solution, for example, from 50 $\mu$L to 1 ml of tetrasodium EDTA adjusted to a pH of 13 with sodium hydroxide. Applicants have found that other treatments for washing a column can also be used alone or in combination with those indicated hereinabove. These treatments include exposing the separation medium to high concentrations of organic solvent (e.g., up to 100% acetonitrile) or exposing the medium to denaturants such as urea (e.g., 5M) or formamide. The column can also be treated by reverse flushing with a washing solution.

The present invention provides a method for detecting mutations in a sample containing a relatively large amount of wild type, wherein the concentration of the mutation is below the limits of detection a detector. Alternatively, the invention provides a method for detecting mutations when the concentration of mutant DNA in a sample may be sufficient to detect, but the mutant DNA is not seen because It is obscured by the relatively large amount of wild type in the sample. The invention takes advantage of the unique and surprising attributes of MIPC and DMIPC to accomplish the objective of detecting mutations in such samples, wherein the wild type and mutant are known.

Preferably, the PCR primers are selected to yield fragments for which complete resolution of heteroduplexes from homoduplexes can be achieved by MIPC. Details for suitable primer selection are provided in copending U.S. patent application Ser. No. 09/129,105 filed Aug. 4, 1998, the entire contents of which are hereby incorporated by reference.

MIPC separates DNA fragments on the basis of their base pair length. The method is highly reproducible. Therefore, columns do not have to be calibrated from sample to sample or from day to day. A DNA fragment of a particular base pair length will elute from an MIPC column at a specific retention time which is reliably reproducible. This characteristic, coupled with the automation, sample collection, and rapid sample analysis capabilities of MIPC make this method uniquely suited for detection of minute quantities of mutations in the presence of a large background of wild type.

Applicants have taken advantage of the reproducible retention time of a particular fragment in MIPC separations to purify and isolate mutant fragments by "blind collection". The term "blind collection" is defined herein to mean the collection of mobile phase flowing through an MIPC column over a specific time interval subsequent to application of a DNA sample to the column. More specifically, "blind collection" refers to collecting mobile phase during the retention time interval corresponding to a previously determined retention time interval of a DNA fragment standard. Since the relationship between MIPC retention time and base pair length is highly reproducible, it is not necessary to detect a desired fragment with a detector in order to know when to collect the fragment. Column mobile phase is simply collected at the predetermined and expected retention time of a desired fragment.

In a preferred embodiment, the invention comprises a number of steps which eliminate any ambiguity regarding the presence or absence of a particular mutant fragment in a sample when the sample contains a large amount of wild type DNA relative to a putative mutation. These steps are described hereinbelow.

Figure 2:
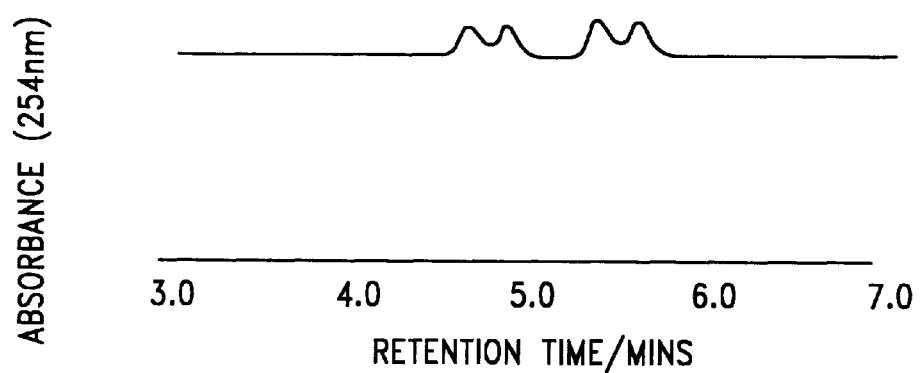
FIG. 2 is a DMIPC chromatogram showing the separation of a standard mixture of FIG. 1.

Since the base sequence of the sample wild type DNA and the putative mutation are known, standards of these materials are combined and hybridized. Hybridization is effected by heating the combined standards to about 90° C., then slowly cooling the reaction to ambient temperature over about 45 to 60 minutes. During hybridization, the duplex strands in the sample denature, i.e., separate to form single strands. Upon cooling, the strands recombine. If a mutant strand was present in the sample having at least one base pair difference in sequence than wild type, the single strands will recombine to form a mixture of homoduplexes and heteroduplexes. In this manner, a standard mixture of homoduplexes and heteroduplexes is formed as depicted schematically in FIG. 1. The standard mixture contains the same homoduplexes and heteroduplexes present in a sample which contains a putative mutation, albeit not in the same ratio. This standard mixture cannot be separated by MIPC under normal conditions, since the heteroduplex and homoduplex have the same base pair length. However, when MIPC is performed at a temperature sufficiently elevated to selectively and partially denature a heteroduplex at the site of base pair mismatch (DMIPC), the partially denatured heteroduplex will separate from a homoduplex having the same base pair length. Therefore, the hybridized standard mixture is applied to a MIPC column and a separation is performed under DMIPC conditions. The chromatogram so produced shows a separation of the homoduplexes and heteroduplexes as shown in FIG. 2. The retention times of the separated homoduplex and heteroduplex standards can then be used to predict the retention times of putative mutations having a concentration too low to be detected by a detector. Alternatively, the retention times of the separated homoduplex and heteroduplex standards can then be used to predict the retention times of putative mutations in samples wherein the mutation signal is obscured by the wild type signal.

Having determined the retention times of the standards, a sample containing a putative mutation is amplified using PCR to increase the total quantity of sample. Since the sequence is known, primers can be designed to maximize the fidelity of replication and minimize the formation of reaction artifacts and by-products. Approaches to primer design and PCR optimization for mutation detection by DMIPC are discussed in co-pending U.S. patent application Ser. No. 09/129,105 filed Aug. 4, 1998. However, wild type and mutant DNA strands in a sample have a nearly identical base sequence. A mutation may contain only one base pair difference compared to wild type. Therefore, primers cannot be designed to selectively anneal to, and preferentially amplify the mutant strand in the presence of wild type. Therefore, when such a sample is amplified using PCR, the ratio of mutant to wild type in the amplified product will be the same as in the original sample.

When the amplified sample is analyzed using MIPC a single major peak will be seen in the resulting chromatogram. This peak represents the combined wild type and mutant DNA, if the latter is present. No separation is achieved because the mutant and wild type DNA have the same base pair length. Therefore, the amplified sample is hybridized and analyzed under partially denaturing conditions by DMIPC. However, the heteroduplex corresponding to the putative mutation, if present, will not be seen by the detector either because its concentration is below the detection limits of the detector or because the ratio of wild type to putative mutation is very large so that the wild type homoduplex peak obscures the heteroduplex peak.

In either case, the heteroduplex corresponding to the mutant DNA in the original sample need not be seen as a chromatographic peak to be determined. Having previously identified the retention time of the heteroduplex standard, the mobile phase is "blind collected" from the column at the expected retention time.

In the operation of the invention, a tissue sample of at least about 100,000 cells is obtained for analysis. It is possible that, despite the initial DNA amplification, there will still be too little heteroduplex to detect. It is also possible that despite the separation of the homoduplex and heteroduplex, some homoduplex may have been collected along with the heteroduplex at the expected heteroduplex retention time, contaminating the heteroduplex and making it difficult to determine without ambiguity whether or not a mutation was present in the original sample. However, the ratio of homoduplex to heteroduplex will now be increased in favor of the heteroduplex compared to the ratio in the original sample.

The "blind collected" mobile phase described hereinabove preferably is concentrated, e.g., by evaporation of the mobile phase. If a mutation was present in the original sample, the residue will now be enriched in the heteroduplex. This heteroduplex enriched residue is amplified again by PCR and the products are hybridized. The hybridized products of the second PCR amplification will now contain an increased amount of heteroduplex relative to homoduplex. This process is described in Example 1 and depicted in FIG. 3. The evaporation can be effected with standard and conventional DNA solution evaporation equipment, for example, the SPEEDVAC evaporator (Model UCS 100 Universal Speed Vac system, Savant Instruments, Inc, Hayward, Calif.)

The steps comprising the method of the invention were designed to enrich the sample in heteroduplex in order to enable the detection of mutations which would normally go undetected. The steps of the method of the invention can be reiterated a plurality of times to increase the purity and quantity of heteroduplex to any desired level. The increased amount of heteroduplex compared to homoduplex obtained in this manner can be described by an "enhancement factor". The "enhancement factor" is defined herein as the increase in the ratio of heteroduplex to homoduplex compared to the ratio of heteroduplex to homoduplex in the original hybridized sample, wherein the increase results from the implementation of the method of the invention. The "enhancement factor" depends on the number of iterations performed and can range from 10 to more than 1,000.

After the final iteration, the PCR product is hybridized and analyzed by DMIPC. If the original sample contained a mutation, the concentration of heteroduplex or its concentration relative to wild type, will now be sufficient to detect. The DMIPC chromatogram will, therefore, show a peak having the retention time of the standard heteroduplex. In this event it can be concluded unambiguously that a mutation was present in the original sample.

As a further confirmation of the identity of the mutation, an aliquot of standard heteroduplex can be mixed with an aliquot of the heteroduplex enriched sample. A DMIPC chromatogram of this mixture will show an increase in the area of the heteroduplex peak, compared to the area of the heteroduplex enriched sample peak alone.

Additionally, the purification and enrichment method described above will provide sufficient heteroduplex for determination of its base pair sequence. Sequencing will provide further confirmation of the identity of the mutation.

If, after performing a plurality of iterations according to the method of the invention as described above no heteroduplex peak is seen in the DMIPC chromatogram, then it can be safely concluded that the original sample did not contain a mutation.

Denaturing gradient gel electrophoresis techniques which can separate homoduplexes from heteroduplexes cannot be used as an alternative to DMIPC. Although samples can be recovered form gels with difficulty, blind collection is not possible because the mobility of a DNA fragment in a gel is not constant. Therefore, its position cannot be reliably predicted. In addition, the shape of DNA fragment bands in gels are often irregular, further complicating sample recovery and making detection uncertain. An additional problem is the fact that gels take many hours to develop, making this method impractical for routine use.

On the other hand, the highly predictable nature of the retention times determined from DMIPC separations make this method uniquely suited to mutation detection if blind collection is required. The use of DMIPC for the purpose of mutation detection as described in this application has not been previously reported.

The detection of cancer cells in early diagnosis screens or in evaluations of a cancer treatment regimen is usually about 1 cancer cell in 100 total cells, or 1%. Thus, cancer cells which are present below the 1% level will not be seen by traditional analytical methods. By providing an enhancement factor of 1000, the present invention increases the sensitivity of cancer cell detection to about 1 cancer cell in 100,000 total cells. Thus, using the method of the invention, the presence of cancer cells can be detected down to a level of about 0.001%. The tremendous extension of the lower limits for cancer cell detection made possible by this invention can save countless lives.

Other features of the invention will become apparent in the course of the following descriptions of exemplary embodiments which are given for illustration of the invention and are not intended to be limiting thereof.

All references cited herein are hereby incorporated by reference in their entirety.

Procedures described in the past tense in the examples below have been carried out in the laboratory. Procedures described in the present tense have not yet been carried out in the laboratory, and are constructively reduced to practice with the filing of this application.

EXAMPLE 1

Mutation detection by "blind collection"

A 191 base pair fragment derived from genomic p53 exon 8 (a PCR product obtained from BioRad, Hercules, Calif.), containing a G to A mutation present in location 138, was hybridized by heating to 90° C. and slowly cooled to ambient temperature over 45 minutes. The top trace of FIG. 3, which is the DMIPC chromatogram of an aliquot of this sample run at 65° C., shows two homoduplex peaks at a retention time of about 6.5 minutes. No heteroduplex can be seen.

Another aliquot of the same sample was chromatographed on the same column and mobile phase was collected between 4.5 and 6.3 minutes. The mobile phase was evaporated to dryness, and the residue was amplified using standard PCR techniques.

Figure 3:
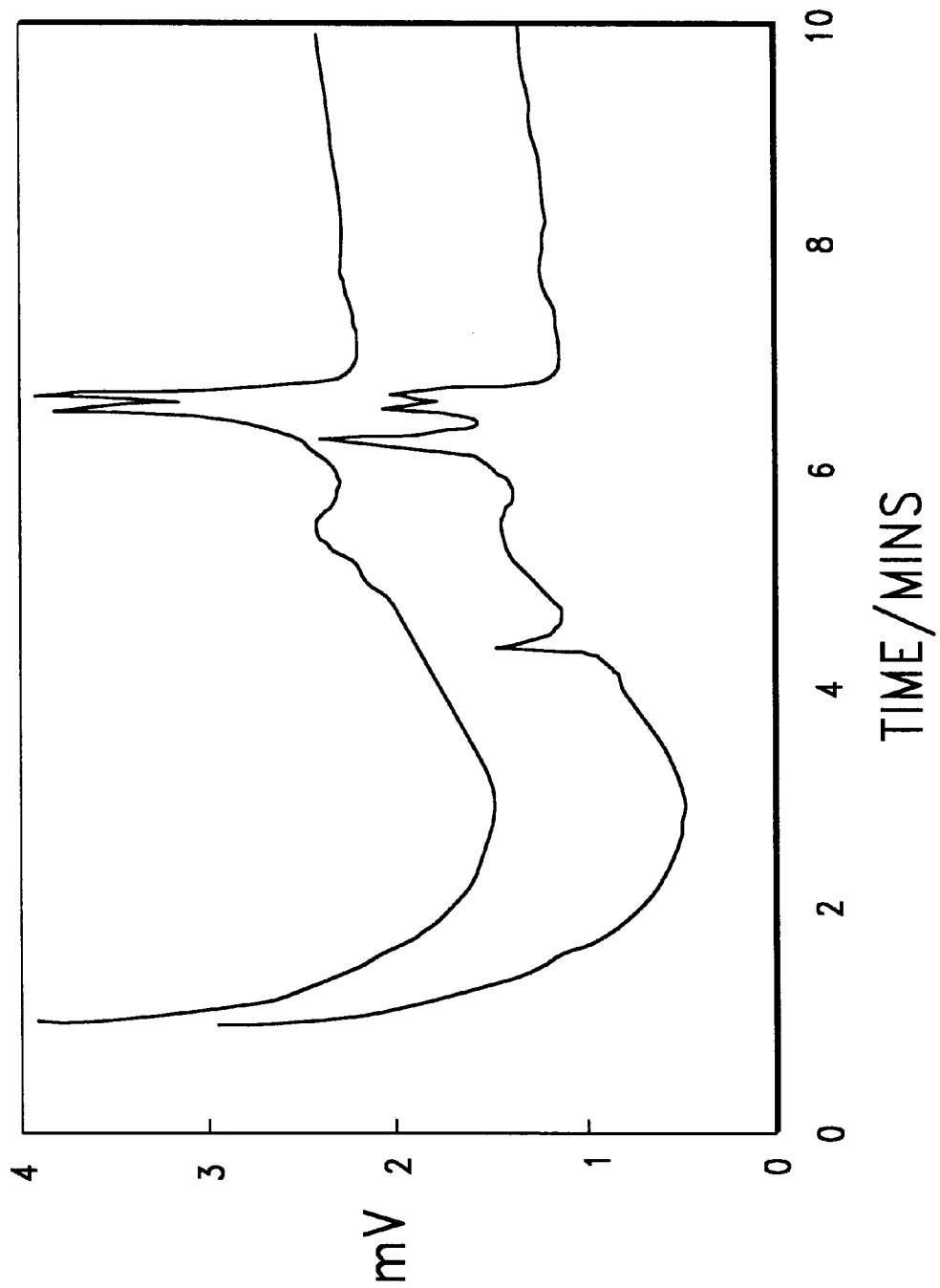
FIG. 3 are DMIPC chromatograms demonstrating mutation detection using blind collection.

The lower trace of the DMIPC chromatogram shown in FIG. 3 now shows a previously undetected heteroduplex peak at a retention time of about 6.2 minutes.

The gradient elution conditions used are shown below:

| Time (min.) | % A | % B |
|---|---|---|
| 0.0 | 48 | 52 |
| 0.5 | 45 | 55 |
| 4.0 | 38 | 62 |
| 5.5 | 0 | 100 |
| 6.5 | 48 | 52 |
| 8.5 | 48 | 52 |

Solvent A: 0.1M triethylammmonium acetate (TEAA)
Solvent B: 25% acetonitrile in 0.1M TEAA
Flow rate 0.9 mL/min.

While the foregoing has presented specific embodiments of the present invention, it is to be understood that these embodiments have been presented by way of example only. It is expected that others will perceive and practice variations which, though differing from the foregoing, do not depart from the spirit and scope of the invention as described and claimed herein.

The invention claims is:

1. A method for preparing a sample of DNA for detecting a putative mutant DNA in said sample of DNA, the method comprising:
   (a) amplifying the sample of DNA using PCR;
   (b) hybridizing the amplified sample to form a mixture of homoduplexes and heteroduplexes;
   (c) separating the product of step (b) into fractions by Denaturing Matched Ion Polynucleotide Chromatography; and
   (d) blind collecting the fractions from step (c) at a retention time corresponding to the retention time of the heteroduplex, wherein said retention time was previously determined from a reference elution profile.

2. A method of claim 1 including amplifying the fractions collected in step (d) using PCR to obtain an increased amount of heteroduplex relative to homoduplex.

3. A method of claim 1 including repeating steps (a) through (d).

4. A method of claim 1 wherein said mutant DNA is below the limit of detection as determined by ultraviolet detection.

5. A method of claim 1 including confirming the identity of the heteroduplex obtained.

6. A method of claim 1 wherein the DNA sequence of the wild type DNA and the mutant DNA are known.

7. A method of claim 1 wherein the mutant DNA differs from wild type DNA by at least one base pair.

8. A method of claim 1, wherein the same primers are used to amplify both the mutant DNA and the wild type DNA in the sample.

9. A method of claim 1 wherein the reference elution profile was obtained by separating a standard mixture of homoduplex and heteroduplex, having the same base pair sequence as the sample, by Denaturing Matched Ion Polynucleotide Chromatography.

10. A method of claim 3 wherein the steps (a) through (d) are repeated until the relative amount of mutant to wild type DNA is increased by an enhancement factor of at least 10 to 1000.

11. A method of claim 1 including confirming the identity of the heteroduplex.

12. A method for screening a tissue sample for cancerous cells by detecting a putative mutant DNA in the DNA of the sample, the method comprising:
   (a) amplifying the DNA of the sample using PCR;
   (b) hybridizing the amplified sample to form a mixture of homoduplexes and heteroduplexes;
   (c) separating the product of step (b) into fractions by Denaturing Matched Ion Polynucleotide Chromatography;
   (d) blind collecting the fractions from step (c) at a retention time corresponding to the retention time of the heteroduplex, wherein said retention time was previously determined from a reference elution profile;
   (e) repeating steps (a) through (d) until the relative amount of mutant to wild type DNA is increased by an enhancement factor of at least 10 to 1000; and
   (f) observing the chromatographic profile obtained during the separation wherein the presence of at least one peak at the retention time of the heteroduplex indicates the presence of said mutant DNA.

13. A method of claim 12 including amplifying the fractions collected in step (d) using PCR to obtain an increased amount of heteroduplex relative to homoduplex.

14. A method of claim 12 including repeating steps (a) through (d) wherein the sample of DNA in step (a) comprises DNA in the fractions collected in step (d).

15. A method of claim 12 wherein said mutant DNA is below the limit of detection as determined by ultraviolet detection.

16. A method of claim 12 including confirming the identity of the heteroduplex obtained.

17. A method of claim 12 wherein the DNA sequence of the wild type DNA and the mutant DNA are known.

18. A method of claim 12 wherein the mutant DNA differs from wild type DNA by at least one base pair.

19. A method of claim 12, wherein the same primers are used to amplify both the mutant DNA and the wild type DNA in the sample.

20. A method of claim 1 wherein the separation of the product by Denaturing Matched ion Polynucleotide Chromatography is effected with an MIPC column containing a stationary phase separation media, and the column is treated before the separating step with a solution for removing any residual DNA from prior separations.

21. A method of claim 20 wherein the column is treated before the separating step with from 50 µL to 1 ml of tetrasodium EDTA adjusted to a pH of 13 with sodium hydroxide.

22. A method of claim 12 wherein the reference elution profile was obtained by separating a standard mixture of homoduplex and heteroduplex by Denaturing Matched Ion Polynucleotide Chromatography, said standard mixture having the same base pair sequence as the amplified DNA.

23. A method of claim 14 wherein the steps (a) through (d) are repeated until the relative amount of mutant to wild type DNA is increased by an enhancement factor of at least 10 to 1000.

24. A method for detecting a putative mutant DNA in a sample of DNA, the method comprising:
   (a) amplifying the sample of DNA using PCR;

(b) hybridizing the amplified sample to form a mixture of homoduplexes and heteroduplexes;

(c) separating the product of step (b) into fractions by Denaturing Matched Ion Polynucleotide Chromatography;

(d) blind collecting the fractions from step (c) at a retention time corresponding to the retention time of the heteroduplex, wherein said retention time was previously determined from a reference elution profile;

(e) repeating steps (a) through (d) until the relative amount of mutant to wild type DNA is increased by an enhancement factor of at least 10 to 1000; and (f) observing the chromatographic profile obtained during the separation wherein the presence of at least one peak at the retention time of the heteroduplex indicates the presence of said mutant DNA.

25. A method of claim 24 wherein the reference elution profile was obtained by separating a standard mixture of homoduplex and heteroduplex, said standard mixture having the same base pair sequence as the amplified DNA, by Denaturing Matched Ion Polynucleotide Chromatography.

26. A method of claim 24 wherein said mutant DNA is below the limit of detection by ultraviolet detection.

27. A method of claim 24 including confirming the identity of the heteroduplex obtained.

28. A method of claim 24 wherein the DNA sequence of the wild type DNA and the mutant DNA are known.

29. A method of claim 24 wherein the mutant DNA differs from wild type DNA by at least one base pair.

30. A method of claim 24 wherein the same primers are used to amplify both the mutant DNA and the wild type DNA in the sample.

* * * * *